(12) United States Patent
van de Voort et al.

(10) Patent No.: US 8,268,624 B2
(45) Date of Patent: Sep. 18, 2012

(54) SYSTEM AND METHOD FOR DETERMINING ACID CONTENT IN LUBRICANTS

(75) Inventors: Frederick R. van de Voort, Edmonton (CA); David Pinchuk, Montréal West (CA)

(73) Assignee: Thermal-Lube, Inc., Pointe-Claire (CA)

( * ) Notice: Subject to any disclaimer, the term of this patent is extended or adjusted under 35 U.S.C. 154(b) by 196 days.

(21) Appl. No.: 12/770,096

(22) Filed: Apr. 29, 2010

(65) Prior Publication Data

US 2011/0269236 A1    Nov. 3, 2011

(51) Int. Cl.
*G01N 31/00* (2006.01)
(52) U.S. Cl. ............ 436/61; 436/60; 436/164; 436/165; 436/166; 436/171
(58) Field of Classification Search .................. None
See application file for complete search history.

(56) References Cited

U.S. PATENT DOCUMENTS 5,889,683 A   3/1999   Ismail et al.

OTHER PUBLICATIONS

The Determination of Acid and Base Number in Lubricants by FTIR Spectroscopy. Van De Voort, F.R., Sedman, J., Yaylayan, V. and Saint-Laurent, C. Applied Spectroscopy 57(11): 1425-1431. (2003).
FTIR Acid and Base Number Analysis: Their Potential to Replace ASTM Methods. Van De Voort, F.R., Pinchuk, D., Davies, M. and Taghizadeh, A. JOAP International Condition Monitoring Conference. (2002).
New FT-IR Methods for Determining Acid Number and Base Numbers in Lubrication. Van De Voort, F.R., Saint-Laurent, C., Sedman, J. and Pinchuk, D. Lubrication and Fluid Power 3(2): 12-16 (2002).
Determination of Total Base Number (TBN) in Lubricating Oils by Mid-FTIR Spectroscopy. Dong, J., Van De Voort, F.R., Yayyalan, Y. and Ismail, A.A. Journal of the Society of Tribologists and Lubrication Engineers 3: 23-29 (2001).
Simple, Rapid and Cost Effective Determination of TAN, TBN and H2O by Differential FTIR Spectroscopy. Van De Voort, F.R., Pinchuk, D. and Pinchuk J. Practicing Oil Analysis. Proceedings of the International Conference and Exhibit Tulsa, OK, USA, Oct. 24-26, 2000. pp. 167-171.
A Novel Method to Determine TAN, TBN and Moisture Using FTIR Spectroscopy. Dong, J., Ismail, A.A. and Van De Voort, F.R. JOAP International Condition Monitoring Conference, FL. (2000).

(Continued)

*Primary Examiner* — Yelena G Gakh
(74) *Attorney, Agent, or Firm* — Gordon & Jacobson, PC

(57) ABSTRACT

A system and method of characterizing an at least partially hydrophobic sample. The method includes providing an ethanolic solution of ethanol and sodium hydrogen cyanamide, adding a first portion of the ethanolic solution to a sample to produce a reagent-sample mixture, performing infrared spectroscopic testing of the reagent-sample mixture to generate mixture absorption data representing at least one absorption characteristic of the reagent-sample mixture, and generating acidity data for the sample based on the mixture data. The system includes a cell for holding and evaluating a sample which is mixed with an ethanolic solution to create a reagent-sample mixture, an infrared spectrometer for measuring light absorption characteristics of the reagent-sample mixture, and a computer equipped with software for analyzing data outputted by the infrared spectrometer and utilizing an empirical model to derive at least one universal calibration equation relating data representing the light absorption characteristics of the reagent-sample mixture to acidity of the sample.

35 Claims, 4 Drawing Sheets

OTHER PUBLICATIONS

Rapid Determination of the Carboxylic Acid Contribution to Total Acid Number of Lubricants by Fourier Transform Infrared Spectroscopy. Dong, J., Van De Voort, F.R., Ismail, A.A., Akochi-Koble, E. and Pinchuk. D. Lubrication Engineering 6:12-20 (2000).

A New Approach to the Determination of Moisture in Hydrocarbon Lubricating Oils by Mid-FTIR Spectroscopy. Dong, J., Van De Voort, F.R., Yaylayan, V. and Ismail, A.A. Journal of the Society of Tribologists and Lubrication Engineers 56(11): 30-37 (2000).

A New Fourier Transform Infrared Method for the Determination of Moisture in Edible Oils; Ahmed Al-Alawi, Frederick R. Van De Voort, Jacqueline Sedman, applied Spectroscopy, vol. 59, No. 10, pp. 1295-1299 (2005).

An Automated FTIR Method for the Routine Quantitative Determination of Moisture in Lubricants: An Alternative to Karl Fischer Titration; Frederick R. Van De Voort, Jacqueline Sedman, Robert Cocciardi, Steve Juneau, Talanta The International Journal of Pure and Applied Analytical Chemistry, vol. 72, Issue 1, Apr. 15, 2007.

Quantitative Moisture Measurements in Lubricating Oils by FTIR Spectroscopy Combined With Solvent Extraction Approach, Eng-Poh Ng, Svetlana Mintova, Microchemical Journal 98 pp. 177-185 (2011).

Automated FTIR Analysis of Free Fatty Acids or Moisture in Edible Oils, Ahmed Al-Alawi et al., JALA, Feb. 2006, pp. 23-29.

Quantitative Determination of Moisture in Lubricants by Fourier Transform Infrared Spectroscopy, F.R. Van De Voort et al., Applied Spectroscopy, vol. 58, No. 2, 2004, pp. 193-198.

Automated Acid Content Determination in Lubricants by FTIR Spectroscopy as an Alternative to Acid Number Determination, D. Li et al., Journal of ASTM International, vol. 6. No. 6, May 2009.

Automated Analysis of Edible Oils and Lubricants by FTIR Spectroscopy: Problems and Solutions, F.R. Van De Voort, presented at Laboratory Automation and Practices: An Overview, Oct. 26, 2006.

SYSTEM AND METHOD FOR DETERMINING ACID CONTENT IN LUBRICANTS

BACKGROUND OF THE INVENTION

1. Field of the Invention

This invention relates broadly to a system and method for compositional analysis of generally hydrophobic products (such as lubricants, edible oils, and fuels) using infrared spectroscopy. More particularly, the invention relates to systems and methods for determining the total acid content of such products using Fourier Transform Infrared (FTIR) spectroscopy.

2. State of the Art

Infrared (IR) spectroscopy is the subset of spectroscopy that deals with the infrared region (e.g., typically including wavelengths from 0.78 to approximately 300 microns) of the electromagnetic spectrum. It covers a range of techniques, the most common being a form of absorption spectroscopy. As with all spectroscopic techniques, it can be used to identify compounds or investigate sample composition. A common laboratory instrument that uses this technique is an infrared spectrophotometer. Infrared spectroscopy exploits the fact that molecules have discrete rotational and vibrational energy levels and absorb infrared light at specific frequencies that are determined by the differences in energy between these discrete energy levels.

In IR absorption spectroscopy, the infrared spectrum of a sample is recorded by passing a beam of infrared light through the sample or placing the sample on the surface of an internal reflection element through which a beam of infrared light is passed by total internal reflection. Measurement of the transmitted or totally internally reflected light striking a detector reveals how much energy was absorbed at each wavelength. This can be done with a monochromatic beam, which changes in wavelength over time. Alternatively, a polychromatic IR beam (e.g., a range of IR wavelengths) can be passed through the sample to measure a range of wavelengths at once. From this, a transmittance or absorbance spectrum can be produced, showing the IR wavelengths at which the sample absorbs. Analysis of these absorption characteristics reveals details about the molecular structure of the sample.

Fourier Transform Infrared (FTIR) spectroscopy is a form of IR absorption spectroscopy that utilizes an interferometer placed between a polychromatic source of IR light and the sample. Measurement of the light striking the detector produces an interferogram. Performing a Fourier transform on the interferogram shows the IR wavelengths at which the sample absorbs. The development of FTIR technology has substantially enhanced the utility and sensitivity of IR spectroscopy as a tool for quantitative analysis. In addition, various data analysis techniques have been developed to facilitate accurate quantitative analysis of highly complex sample mixtures subjected to IR spectroscopic examination. The information inherent in the infrared spectrum of such sample mixtures includes information at the molecular level about the chemical composition of the mixture. Thus, FTIR technology and analysis allows for the determination of the concentrations of the components in the sample mixture, and for the detection of contaminants or other unwanted chemical components or compounds in the sample mixture.

One area in which FTIR spectroscopy has been extensively utilized is in the monitoring of the condition of lubricating fluids, an activity which has commonly been performed in commercial laboratories. For example, FTIR spectroscopy has been employed to monitor the levels of additives present in such fluids and of degradation products that may be generated as a result of breakdown of the fluid. In another example, the amount of water present in lubricating oils has been quantitated by means of a "splitting" method that utilizes a stoichiometric reaction between water and 2,2-dimethoxypropane (DMP) to produce acetone, a product which is readily measured by IR spectroscopy. This splitting method includes diluting an oil sample and splitting it into two parts. One of the two parts is treated with a blank reagent. The other part is treated with a reactive reagent (DMP). Both parts are then analyzed using FTIR spectroscopy, and moisture measurements are obtained by subtracting the spectrum of the sample treated with the blank reagent from the spectrum of the sample treated with the reactive reagent to eliminate the spectral features of the oil, leaving only the spectral changes related to the reaction. This FTIR method was an improvement over the ASTM Karl Fischer (KF) titration method, a methodology commonly used to measure water in oil samples. It allowed the amount of moisture in an oil sample to be quantified while avoiding the limitations of the KF method, such as its susceptibility to oil additive interferences that affect the accuracy and precision of the data obtained.

Another area in which FTIR spectroscopic analysis has found application is in the analysis of edible fats and oils employed in the food industry, which are extracted from a wide range of raw materials and then refined and processed in various ways, for example, by fractionation and hydrogenation. In "*Automated FTIR Analysis of Free Fatty Acids or Moisture in Edible Oils*" (McGill University, Quebec Canada, JALA February 2006), a methodology for analyzing the free fatty acid content of edible oil mixtures is disclosed. The method utilizes methanol as the reagent solvent (which is completely immiscible with the edible oil) and employs NaHN—C≡N as a reagent to convert free fatty acids into methanol-soluble salts without causing saponification of the oils. This method includes thoroughly mixing an edible oil sample with the reagent solvent, allowing the mixture to stand to ensure separation of the oil and solvent layers, and then analyzing the free fatty acid content using FTIR analysis. As the edible oils being analyzed in this process are completely immiscible with the reagent solvent (methanol), interferences due to absorption of the IR light by the oil portion of the sample do not pose an issue in the analysis.

SUMMARY OF THE INVENTION

The present invention is directed to a system and method for generating data characterizing the total acid content (e.g., the total amount of organic acid and inorganic acid), as well as the individual proportions/concentrations of organic acid and inorganic acid present in fluids which are predominantly hydrophobic in nature. In particular, the system includes an infrared spectrometer, a cell for holding and evaluating a sample, and a computer or workstation equipped with data analysis software for analyzing the data measured by the infrared spectrometer. The system can also include equipment for facilitating manual and/or automated operation of the infrared spectrometer, sample testing, and data collection.

The method of the present invention includes preparing or providing a solution (referred to below as the "ethanolic reagent solution," "reagent solution" or "reagent") of ethanol (ethyl alcohol) and sodium hydrogen cyanamide (NaHN—C≡N), and adding the reagent solution to a generally hydrophobic sample, whereby the reagent solution reacts stoichiometrically with acidic components, if any, present in the sample, to produce a reagent-sample mixture. The infrared spectrometer and the data analysis software executing at the workstation are used to perform IR spectroscopy on the reagent-sample mixture. The data analysis software generates data that characterizes the total acid content and the individual amounts/concentrations of organic and inorganic acid in the sample by processing the absorption characteristics of the reagent-sample mixture as derived from the IR spectroscopy (preferably, the absorption characteristics of the reagent-sample mixture at or near the 2109 cm$^{-1}$ and 1571 cm$^{-1}$ wavelengths). In the preferred embodiment, the empirical model and data analysis software characterize the concentration or quantity of organic and inorganic acids, if any, present in the sample. In the preferred embodiment, the sample's total acidity is characterized by data calculated from the absorption change of the reagent-sample mixture at or near the 2109 cm$^{-1}$ wavelength when the NaHN—C≡N in the reagent solution reacts with the acidic components in the sample to form cyanamide $H_2$N—C≡N. In this manner, the NaHN—C≡N of the reagent solution serves as a "signal-transducing reagent" for determining total acid content. The absorption change between the reagent solution and the reagent-sample mixture at or near the 2109 cm$^{-1}$ wavelength is representative of the amount of base consumed by the acid-base reaction. The amount of base consumed is directly proportional to the total acid content which was originally present in the sample and extracted therefrom by the ethanolic reagent solution.

In the preferred embodiment, the apportionment of organic acid and inorganic acid which comprise the total acid content of the sample is determined by measuring the absorption characteristics of the reagent-sample mixture at or near the 1571 cm$^{-1}$ wavelength. In particular, if the sample contains organic acid, then the reaction between the organic acid in the sample and the reagent solution (a base) will cause the reagent-sample mixture to absorb IR light at or near 1571 cm$^{-1}$. In this manner, the absorbance of the reagent-sample mixture at the 1571 cm$^{-1}$ wavelength is used to derive data characterizing the sample's organic acid content. The inorganic acid content of the sample may then be simply derived by subtracting the organic acid content from the total acid content of the sample.

In the preferred embodiment, the empirical model used to characterize the organic acid content, inorganic acid content, and total acid content of the sample is derived by a calibration process in which varying amounts of any medium to long-chain (e.g., $C_8$-$C_{18}$) carboxylic acid, but preferably oleic acid ($C_{17}H_{33}$COOH), are added to equal portions of the reagent solution to form calibration standards. Oleic acid is preferred because it is liquid, soluble, and easy to handle. A unit acidity value (e.g., a representation of the concentration of the total acid present per unit volume, expressed in mEq Acid/mL) is calculated for each of the calibration standards. The reaction between the carboxylic acid and the ethanolic reagent solution results in absorption changes between the reagent solution and each calibration standard at 2109 cm-1 and at 1571 cm-1. The unit acidity values of the calibration standards (e.g., the total unit acidity and the organic unit acidity of each of the calibration standards) are then plotted against their respective measured absorbance values at 2109 cm-1 and 1571 cm-1, preferably measured after taking a 5-5 gap-segment 2nd derivative of the absorption data. Linear regression of this data is used to derive universal calibration equations. The universal calibration equations represent the standard curve of the universal calibration of the reagent solution (e.g., its acid reducing capacity), expressed in terms of unit acidity. As discussed below, these equations are used to calculate the total unit acidity and the organic unit acidity of a sample as a function of the observed absorbance values of a reagent-sample mixture at the 2109 cm-1 and 1571 cm-1 wavelengths, respectively.

The values for the total unit acidity and the organic unit acidity of the sample are multiplied by the volume of the reagent solution that is combined with a sample, and divided by the weight of the sample to yield sample data characterizing the organic acid content and total acid content in units of mEq Acid/g sample. Data characterizing the inorganic acid content of the sample is obtained by subtracting the sample's organic acid content from its total acid content.

In the preferred embodiment, the empirical model accounts for i) density changes which may occur when the sample is added to the reagent solution, and ii) miscibility, if any, of the sample within the reagent solution. The empirical model preferably accounts for these effects by measuring the absorbance of both the reagent solution and the reagent-sample mixture at 1924 cm-1 relative to a single-point baseline at 1859 cm-1. Absorption at the 1924 cm-1 wavelength of ethanol is measured because interfering absorptions in this region of the IR spectrum are rare. This absorption data allows for the calculation of a density/dilution correction factor. The spectrum of the reagent-sample mixture is then multiplied by the density/dilution correction factor. A differential spectrum is then calculated by subtracting the spectrum of the reagent solution from the density/dilution factor-corrected spectrum of the reagent-sample mixture. The absorbance values of the reagent-sample mixture at or near the 2109 cm-1 and the 1571 cm-1 wavelengths, respectively, are measured from this differential spectrum as per calibration, preferably after taking a 5-5 gap-segment 2nd derivative of the absorption data.

Advantageously, the present method may be utilized to characterize the content of both organic and inorganic acids in a sample. As further discussed below, by extracting the acidic components present in the oil sample with the oil-immiscible signal-transducing reagent (NaHN—C≡N in absolute ethanol), spectral interferences from the oil during FTIR analysis are eliminated rather than compensated for by differential spectroscopy, a process discussed above which required splitting the sample. The combined extraction/signal-transduction approach of the present invention can provide substantial gains in sample analytical throughput for a given system.

According to one aspect of the invention, when samples are used which are miscible with the reagent solution, matrix effects which occur, if any, may also be accommodated by performing a spectral analysis of a sample-blank.

According to another aspect of the invention, the method provides the flexibility to modify the analytical range and sensitivity of the calibration and/or analyses by simple adjustment of the calibration/sample weights, reagent volumes, or combinations thereof.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
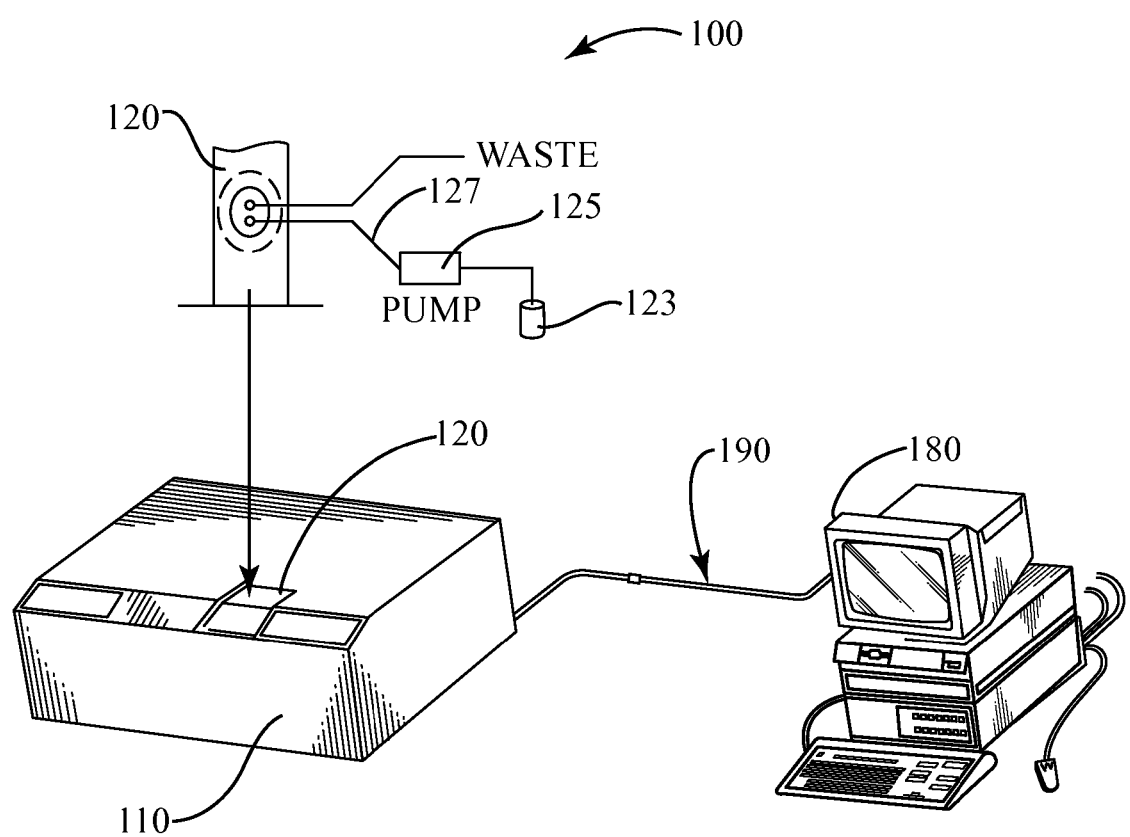
FIG. 1 is a schematic view of a system for performing IR analysis in accordance with the present invention.

Turning to FIG. 1, a system 100 for performing spectroscopic analysis of a sample includes a spectrometer 110 for collecting IR absorption data. A WorkIR series IR spectrometer 110 (which is preferably equipped with a deuterated triglycine sulfate (DTGS) detector) as sold commercially by ABB Analytical of Quebec, Canada can be used. Other commercially-available FTIR spectrometers can also be used. A sample cell 120 is provided into which a sample (e.g., a sample in a vial) may be loaded annually, such as by aspiration into the cell 120, or in an automated manner with a minipump used in conjunction with an autosampler (not shown). A 100-μm $CaF_2$ transmission flow cell is preferably utilized. As schematically shown in FIG. 1, a sample 123 is pumped into the cell 120 via a pump 125 through an in-line 127. A disposal waste line 129 extends out of the cell 120. Data acquired by the spectrometer 110 is communicated to a computer or workstation 180 via a data interface 190 (e.g., USB data interface or the like) for processing and analysis in accordance with the present invention. The computer 180 preferably includes a complete and fully integrated software package which is run at the computer 180 for analyzing the data and outputting information to a user (e.g., via a printer and/or on-screen). The software should at a minimum be able to perform basic IR data acquisition, analysis, and quantification.

In the preferred embodiment, the spectral acquisition parameters for the apparatus 100 are set to the following:
  resolution—4 $cm^{-1}$;
  apodization—triangular;
  gain—1; and
  number of co-added scans—32 or 16, depending on whether the spectrometer 110 collects single-sided or double-sided interferograms).
The spectral acquisition time should be approximately 32 seconds.

Figure 2:
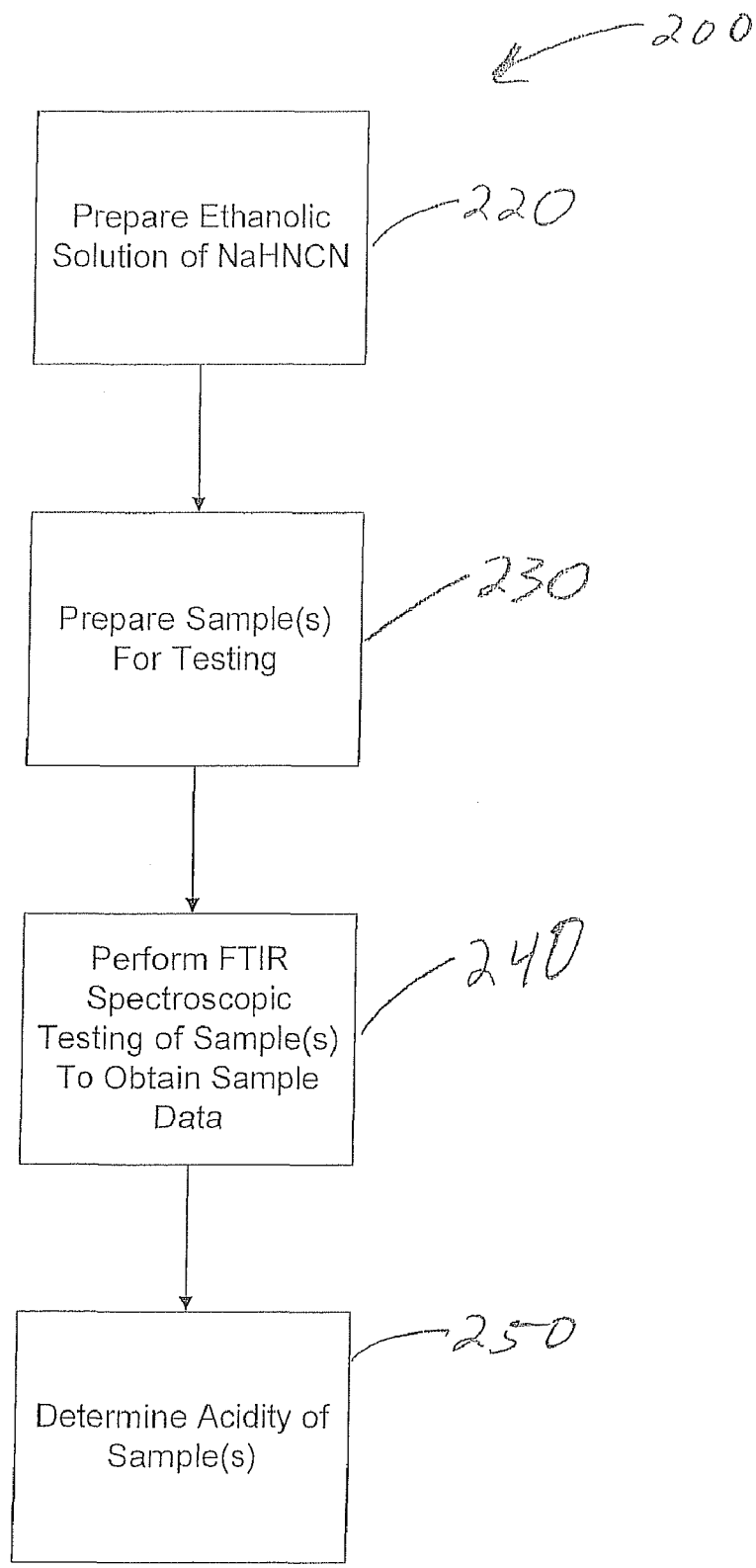
FIG. 2 is a flowchart showing the overall method steps of the present invention.

The system 100 is used to perform the method 200 of FIG. 2 for generating data characterizing the organic acid content, inorganic acid content, and total acid content in various types of generally hydrophobic samples in accordance with the present invention. The method 200 is based on the extraction of the acids present in a given sample into an ethanolic reagent solution of the base NaHN—C≡N, which serves as a "signal-transducing" reagent. By extracting the acids present in the oil sample into the oil-immiscible signal-transducing reagent, the present method simplifies earlier methodologies by eliminating spectral interferences from the oil rather than compensating for them by differential spectroscopy.

As shown in FIG. 2, the method begins at block 220 with the preparation of an ethanolic reagent solution of sodium hydrogen cyanamide (NaHN—C≡N), a spectrally measurable base. This reagent solution may be immediately used after it is prepared or sealed to minimize exposure to air and moisture, in which case the reagent solution should also be refrigerated. Moisture is readily drawn into the reagent solution from the air, and, in combination with $CO_2$, steadily produces sodium carbonate as well as cyanamide $H_2N$—C≡N over time, which results in a decrease of the acid neutralizing capacity of the reagent solution. Sealing and refrigerating the reagent solution dramatically reduce the loss of NaHN—C≡N over time. If any insoluble material becomes apparent during storage, then the reagent solution should be re-filtered or decanted before using it. Prior to using the reagent solution, and prior to using any re-filtered and decanted reagent solution, the reagent solution's FTIR spectrum should be recorded and its absorbance value at IR wavelength 2109 $cm^{-1}$ checked using the FTIR system 100.

The prepared reagent solution will have an acid-neutralizing capacity (ANC), which may be represented as the number of moles of base reagent present per liter of solution, calculated as follows:

$$ANC = C/M \quad (1)$$

where C is the concentration of base per liter of solution (g/L) and M is the mass of one mole of the base reagent (g/mole). Thus, ANC is a reflection of the moles of base present per liter of solution, and can also be expressed as millimoles per milliliter of solution, or mEq Acid/ml of solution, the Unit Acidity (UA).

The total acid-neutralizing capacity (TNC) of the reagent solution of NaHNCN used with respect to each sample analyzed (further discussed below) will vary in accordance with the volume (V) of the reagent solution used with respect to each sample:

$$TNC = ANC * V \quad (2)$$

At block 230, a quantity of the reagent solution is added to one or more samples to be tested to produce reagent-sample mixtures. If any acid is present in a given sample, then the ethanolic reagent solution will react with it when added to the sample. In particular, the strong C≡N wavelength, which is observable at 2109 $cm^{-1}$ in the spectrum of the reagent solution of sodium hydrogen cyanamide (NaHN—C≡N), will respond proportionately to any acid present in the sample. The NaHN—C≡N present in the reagent solution thus serves as a signal-transducing reagent during FTIR testing and collection of spectroscopic data.

The ethanolic reagent solution will thus exhibit an easily measurable change in the NaHN—C≡N wavelength between the reagent solution and the reagent-sample mixture sample that represents the amount of base consumed by the acid-base reaction in the reagent-sample mixture. It will be appreciated, then, that the total acid content of the sample can be determined by extraction of the acid in the sample with the ethanolic reagent solution of NaHN—C≡N of appropriate concentration (e.g., dependent on the maximum amount of acid potentially in the sample) followed by a measurement of the change in the C≡N band in the spectrum of the reagent-sample mixture.

To this end, at block 240, the system 100 is used to perform FTIR spectroscopic testing of the reagent-sample mixtures, and to record the absorption characteristics associated therewith (e.g., as further discussed below with respect to FIG. 3), preferably the absorption characteristics of the reagent-sample mixture at or near the 2109 $cm^{-1}$ wavelength (e.g., in the range of 2105 $cm^{-1}$ to 2115 $cm^{-1}$) to calculate total acid content of the sample and at or near the 1571 $cm^{-1}$ wavelength (e.g., in the range of 1565 $cm^{-1}$ to 1575 $cm^{-1}$) to calculate organic acid content of the sample.

At block 250, an empirical module is utilized to characterize the sample's acid content (e.g., the organic acid content, inorganic acid content, and total acid content of the sample) based on the absorption characteristics of the reagent-sample mixtures measured during the FTIR spectroscopic testing at block 240. In the preferred embodiment, calibration equations are utilized to determine the total unit acidity (TUA) and organic unit acidity (OUA), respectively, for a sample as a function of the observed change in absorbance values in the infrared spectrum of the reagent solution at the 2109 cm$^{-1}$ and 1571 cm$^{-1}$ wavelengths when the samples are added thereto. The inorganic unit acidity of the sample is determined by subtracting the organic unit acidity from the total unit acidity. The total unit acidity, organic unit acidity, and inorganic unit acidity values of the sample may then be converted to acid content (AC), organic acid content (OAC), and inorganic acid content (IAC), respectively.

Figure 3:
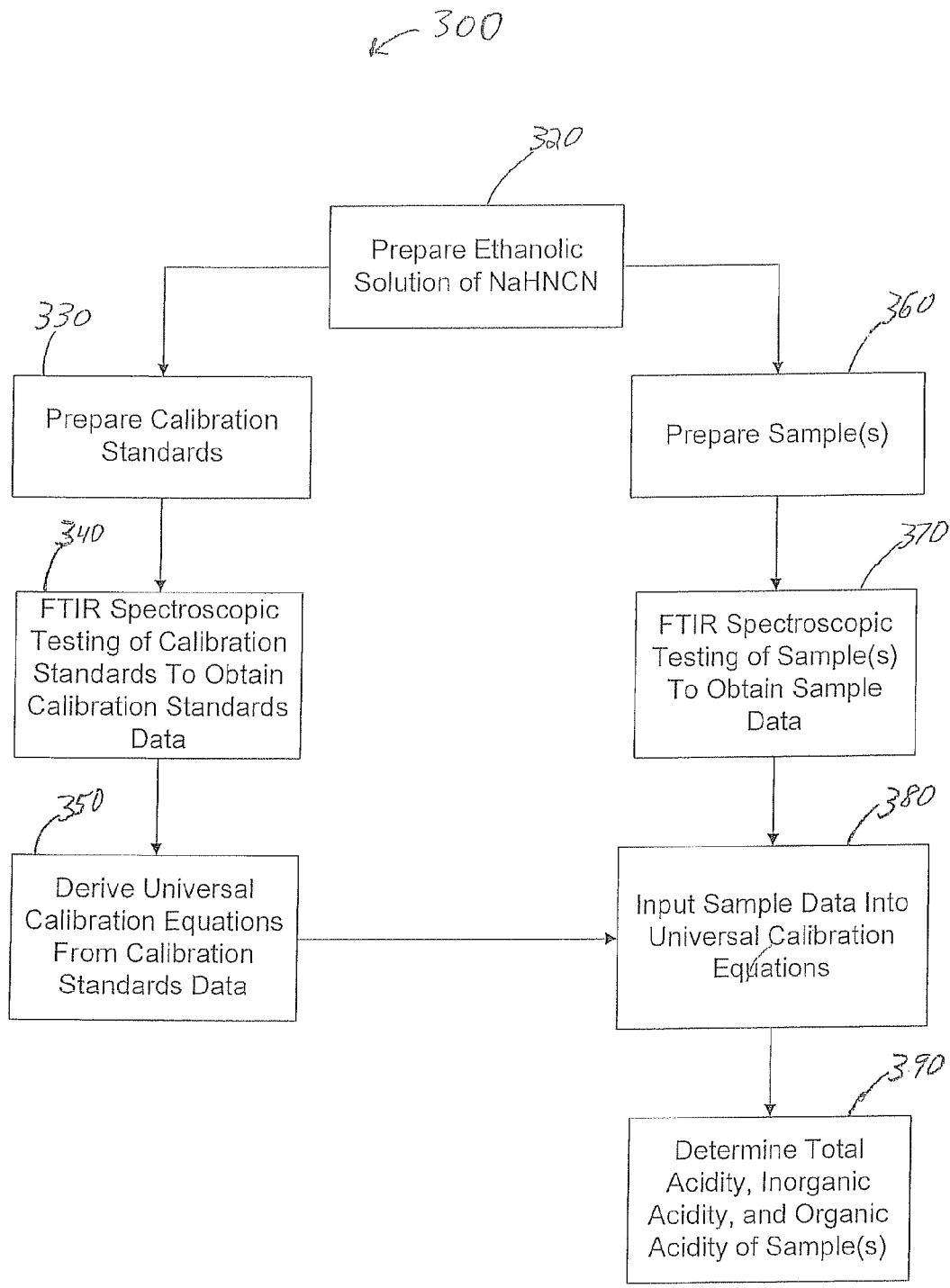
FIG. 3 is a flowchart showing the method steps of a preferred embodiment of the present invention.

A preferred embodiment of the above described method which utilizes a specific calibration protocol and an empirical model for relating absorbance values measured at both the 2109 cm$^1$ and 1571 cm$^{-1}$ wavelengths to the sample's organic acid content, inorganic acid content, and total acid content is described below with respect to FIG. 3. The method uses 15 mL of ethanolic reagent solution and 4 grams of sample and can be used for testing samples which have a total acid content of up to approximately 0.08 mEq acid/gram (e.g., the equivalent of 4.9 mg KOH/gram).

At block 320, the preferred method 300 begins with the preparation of the ethanolic reagent solution of sodium hydrogen cyanamide (NaHN—C≡N), preferably using commercial monosodium hydrogen cyanamide (such as 98%—Sigma-Aldrich from Oakville, ON, Canada. CAS No. 17292-62-5. Mw=64.02). In a one-liter volumetric flask, approximately two and a half grams of NaHN—C≡N are weighed and brought to volume with anhydrous ethanol, preferably using commercial alcohols of Brampton, ON, Canada. An accurate weighing of the two and a half grams of NaHN—C≡N is not required because, as further discussed below, all spectral measurements which are used for calibration and sample analysis in the preferred method 300 are made relative to a reagent blank, and thus are independent of the specific concentration of NaHN—C≡N in the reagent solution. The specific concentration of NaHN—C≡N in the reagent solution defines the overall acid-neutralizing capacity of the solution. However, concentrations greater than 2.5 grams/liter are not recommended as the solubility of NaHN—C≡N in ethanol is limited, and its sensitivity to $CO_2$ and moisture is substantially increased at concentrations greater than 2.5 grams/liter.

A magnetic stirring plate and stirrer are preferably utilized to vigorously stir the ethanolic reagent solution for 20 minutes to dissolve the NaHN—C≡N. Using a glass funnel, the solution is filtered through Whatman #1 filter paper (12.5 cm) into a 1 liter clear glass bottle to remove any residual insolubles. Commercial NaHNCN is approximately 98% pure—the main impurity will be sodium carbonate.

The absorbance of a freshly prepared 2.5 g/L solution of NaHN—C≡N when recorded in a 100-μm transmission cell should be approximately 400 milliabsorbance units (0.40 absorbance units) at 2109 cm$^{-1}$ relative to a single-point baseline at 1859 cm$^{-1}$. If the ethanolic reagent solution has been refrigerated for some time, and its absorbance value drops more than 10% from that of the freshly prepared solution, then a new reagent solution should be prepared.

The acid-neutralizing capacity (ANC) of 2.5 g NaHN—C≡N per liter of the freshly prepared ethanolic reagent solution is, in accordance with Equation (1), approximately 0.039 mEq/mL of reagent. It will be appreciated that this ANC can be expressed in equivalent terms of a quantity of, for example, KOH, by multiplying the molecular weight of KOH (56.11 g/mol) by 0.0390 moles/L, which equals 2.19 g KOH/L or 2.19 mg KOH/mL.

Thus, for example, using 1 ml, 15 ml, 20 ml, and 25 ml of the reagent solution would, in accordance with Equation (2), be expected to produce the total neutralizing capacity (TNC) values shown in Table-1:

TABLE 1

| Volume of reagent used (mL) | 1 | 15 | 20 | 25 |
|---|---|---|---|---|
| Total acid neutralizing capacity (mEq acid) | 0.039 | 0.585 | 0.781 | 0.976 |
| Total acid neutralizing capacity (mg KOH) | 2.19 | 32.82 | 43.82 | 54.76 |

After preparing the reagent solution of NaHN—C≡N at block 320, a universal calibration process is preferably performed. The universal calibration process is represented from block 330 to block 350 and utilizes a standardized protocol for a medium-range calibration based on the use of 15 mL of the reagent solution. At block 330, calibration standards are prepared by applying various quantities of pure oleic acid (preferably 99%—Fisher Chemical, Fair Lawn, N.J. Mw=282.4614) directly to aliquots of the ethanolic reagent solution of NaHN—C≡N. Specifically, approximately 10, 20, 40, 60, 80 and 100 mg portions of the oleic acid are weighed out and placed into corresponding 30-mL glass vials on an analytical balance. The weight of the oleic acid in each of the 30-mL vials is recorded to 4 decimal places. The concentration of oleic acid is herein expressed as mEq Acid/mL and is termed Unit Acidity (UA). As discussed below, the Unit Acidity is universal in that it is independent of the sample weight and reagent volume used in the analysis of samples.

Next, 15 mL of the reagent solution (the ethanolic reagent solution of NaHN—C≡N) is added to each of the 30-mL glass vials using a calibrated, preset pro-pipette. A 50-mL Propipette reagent dispenser (e.g., Eppendorf, Fisher Scientific, Ottawa, ON, Canada) may be utilized. Each vial is capped and then vortexed for 30 seconds. It will be appreciated that the oleic acid reacts with the ethanolic solution according to the following: RCOOH+NaHNCN→RCOO$^-$ Na$^+$+H$_2$NCN.

At block 340, FTIR spectroscopic testing and analysis is performed on the calibration standards using the FTIR system 100 to obtain the IR absorption data from which to derive universal calibration equations. In particular, each calibration standard's absorption characteristics at the 2109 cm$^{-1}$ and 1571 cm$^{-1}$ wavelengths are measured as follows. An open-beam background spectrum is initially collected. Next, the cell 120 is rinsed with the reagent solution (RS). The reagent solution is then loaded into the cell 120 and its spectrum is collected and the spectrum of each calibration standard ($C_{1...n}$) is then acquired, saved, and processed as follows.

First, the absorbance value of the ethanol IR absorption wavelength at 1924 cm$^{-1}$ relative to the absorbance value at a single-point baseline at 1859 cm$^{-1}$ (designated Abs$_{1924/1859\ cm-1}$) is preferably measured in the spectrum of the reagent blank (RB) (e.g., in the spectrum of the reagent ethanolic solution prepared at block 320) and in the spectrum of each calibration standard ($C_{1...n}$) prepared at block 330. The reason for this is to calculate a density correction factor to account for any changes in the density of the reagent solution upon addition to it of oleic acid (further discussed below with respect to blocks 370 and 390).

The density correction factor (DCF) for each calibration standard ($C_x$) is calculated by dividing the value of Abs$_{1924/1859\ cm-1}$ for the reagent blank (RB) by that for the standard:

$$DCF = A_{RB}/A_{Cx} \quad (3)$$

where $A_{RB}$ is the value of $Abs_{1924/1859\ cm^{-1}}$ for the reagent blank, and $A_{Cx}$ is the value of $Abs_{19241/859\ cm^{-1}}$ for the corresponding calibration standard.

The spectrum of each standard is then multiplied by its DCF value (to correct for any density change relative to the reagent solution) and saved as a corrected calibration spectrum ($Cc_x$):

$$Cc_x = C_x * DCF \quad (4)$$

The spectrum of the reagent blank (RB) is then subtracted from each corrected calibration spectrum ($Cc_x$) to obtain the differential spectrum ($Ccd_x$):

$$Ccd_x = Cc_x - RB \quad (5)$$

The 5-5 (gap-segment) second derivative of the differential spectrum ($Ccd_x$) for each calibration standard is then computed as follows. First, the absorbance value $A(i)$ at each data point i of the spectrum is replaced by the mean absorbance value for a segment of 5 data points centered at data point i by:

$$A(i) = [A(i-2) + A(i-1) + A(i) + A(i+1) + A(i+2)]/5 \quad (6)$$

A gap second derivative is then applied at each data point i by:

$$d^2A(i)/dx^2 = [-2A(i) + A(i+2g) + A(i-2g)]/4g\Delta x \quad (7)$$

where $\Delta x$ is the data point spacing in units of wavenumbers and g is set to 5 for the 5-5 (gap-segment) second derivative. The result at each data point i is multiplied by 100 to produce the final calibration spectrum $Cf_x$. It is noted that measurements made on this second-derivative spectrum are referred to as absorbance (Abs) measurements for the sake of simplicity.

For each final calibration spectrum $Cf_x$, the absorbance values at the 2109 $cm^{-1}$ wavelength ($Abs_{2109\ cm^{-1}}$) and at the 1571 $cm^{-1}$ wavelength ($Abs_{1571\ cm^{-1}}$) are then measured. These measurements facilitate calculating and plotting the unit acidity (UA) values of the calibration standards (e.g., the total unit acidity and organic unit acidity), calculated from the weights of oleic acid used to prepare them, against their measured absorbance values ($Abs_{2109\ cm^{-1}}$ and $Abs_{1571\ cm^{-1}}$), and obtaining the universal calibration equations for total unit acidity (TUA) and organic unit acidity (OUA), respectively, by linear regression as follows.

At block 350, the universal calibration equations are derived from the $Abs_{2109\ cm^{-1}}$ and $Abs_{1571\ cm^{-1}}$ values of the calibration standards measured at block 340. In particular, a number of calculations are required to develop the standard curve for the universal calibration of the reagent solution in terms of Unit Acidity (UA). First, the UA for each calibration standard of oleic acid (e.g., for each of the six vials of oleic acid) is determined:

$$UA_{1-n} = W_{1-n}/(V_{1-n})(O) \quad (8)$$

where UA is the Unit Acidity for each standard of oleic acid, expressed in mEq acid/mL reagent solution; W is the weight, expressed in mg, of oleic acid for each standard; V is the volume of reagent ethanolic solution, expressed in mL, added to the oleic acid; and O is the molecular weight of the oleic acid (282.46 g/mol).

Figure 4:
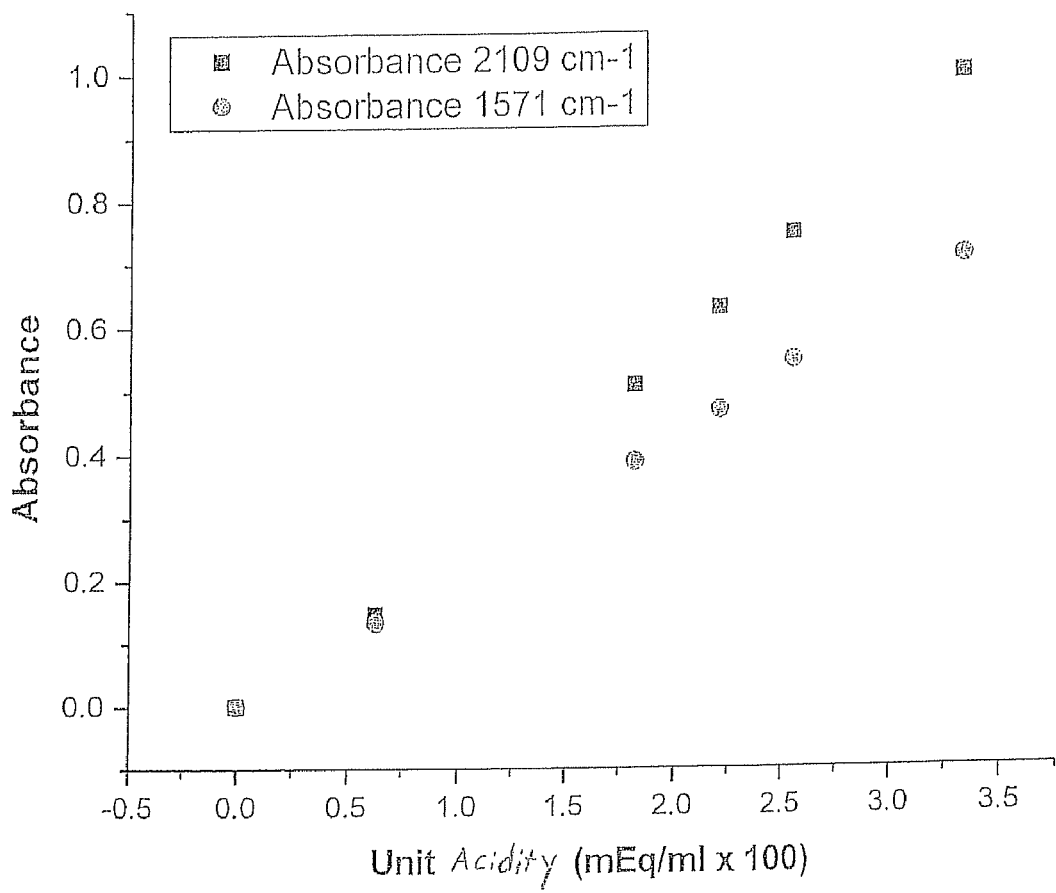
FIG. 4 shows a sample graph of the unit acidity values for the calibration standards plotted against the corresponding absorbance values of the calibration standards measured at two IR wavelengths.

As shown in FIG. 4, the $UA_{1-n}$ values obtained for each of the calibration standards are plotted against their respective $Abs_{2109\ cm^{-1}}$ and $Abs_{1571\ cm^{-1}}$ values, and linear regression is used to obtain the best fit calibration equations for the determination of total unit acidity (TUA) and organic unit acidity (OUA), respectively. Total unit acidity is a representation of the total acidic components (organic plus inorganic) per unit volume, and organic unit acidity represents only the organic acidic components per unit volume and does not include inorganic acidic components per unit volume. FIG. 4 shows typical medium-range calibration plots based on the standard protocol discussed herein using the 100-um cell 120. TUA and OUA values are calculated as follows:

$$TUA = a + b * A_{2109/2109\ cm^{-1}} \quad (9)$$

$$OUA = c + d * A_{1571/1571\ cm^{-1}} \quad (10)$$

where the total unit acidity, TUA, is expressed in mEq acid/mL, and the organic unit acidity, OUA, is expressed in mEq acid/mL, 'b' and 'd' are the slopes of the respective best fit lines, and 'a' and 'c' are the respective values at which the respective best fit lines cross the 'y' axis. The calibration equations (9) & (10) are used to calculate the acid content of the samples (further discussed below with respect to blocks 380-390) after procurement and testing of the samples. It will be appreciated that the universal calibration is based on unit acidity ([$H^+$]) expressed as mEq acid/mL, rather than mmol acid/mL given that samples may contain diprotic or polyprotic acids.

At block 360, a plurality of generally hydrophobic samples to be tested (e.g., oil, lubricant, edible oil, or fuel samples) are prepared for analysis. Four grams of each sample are placed into a respective tared 30-mL screw-cap glass vial and weighed on an analytical balance. The samples' weights are each recorded to four decimal places. The 30-mL screw-cap glass vials used may be, for example, those displayed in catalog #03-339-22H of Fisher Chemical in Fair Lawn, N.J., and/or centrifuge tubes equipped with Mylar-lined septum caps.

If a sample happens to be fully or partially miscible with the ethanolic reagent solution, and if there is evidence that this miscibility may interfere with the FTIR measurements of TUA and/or OUA, then a sample-blank should also be prepared. As the test method 200, 300 disclosed herein uses a gap-segment second derivative to minimize spectral interferences, preparation of a sample-blank will not be necessary in most circumstances. However, for certain types of sample materials (e.g., phosphate esters) which produce spectral interferences that are not completely eliminated by the gap-segment second derivative, a sample blank is utilized (further discussed below). The sample blank is prepared by weighing out approximately the same amount of sample into an additional 30-mL vial.

Still referring to block 360, fifteen milliliters of the ethanolic reagent solution are added using a calibrated, preset pro-pipette to each vial containing a sample. The vial is then capped and must be hermetically sealed in order to prevent moisture and $CO_2$ from reacting with the NaHN—C≡N. The cap should be fitted with a Mylar liner to allow the sample to be aspirated into the IR cell 120 by puncturing the Mylar liner ether manually using a syringe needle or with an autosampler needle in an automated mode. These precautions are important as the measurement of total unit acidity (TUA) of a reagent-sample mixture is made by difference relative to the reagent solution, such that any consumption of NaHN—C≡N by an extraneous reaction (either in the reagent blank or in the sample) will result in erroneous AC values. If a sample-blank is prepared, the same volume of anhydrous ethanol is preferably added to the additional vial.

Once all of the reagent-sample mixtures (and sample-blanks) have been prepared, the reagent-sample mixture vials are shaken on a reciprocal shaker, such as a bench-top horizontal shaker, for a minimum of thirty minutes. The reagent-sample mixture vials are then allowed to stand for ten minutes; alternatively, the reagent-sample mixtures may be centrifuged for a minimum of five minutes at approximately 5000×g in a clinical centrifuge. It is noted that upon addition of the reagent solution to the samples in their respective vials, most of the reagent-sample mixtures should immediately partition with the ethanol phase disposed at an upper layer.

However, the reagent-sample mixtures should be allowed to stand (or centrifuged) in order to ensure complete separation of the two phases. It is noted that some reagent-sample mixtures will not partition into two phases because the sample is fully miscible with the reagent solution. As discussed above, if a sample is fully or partially miscible with the reagent solution, then preparation of a sample-blank should be considered.

At block 370, each of the reagent-sample mixtures prepared at block 360 is tested using the IR system 100. Portions are taken from approximately the upper twelve mL of each reagent-sample mixture vial (e.g., from the portion disposed at the upper layer). The upper layer will be ethanol if the sample is immiscible, predominately ethanol if it is partially miscible, and a mixture of oil and ethanol if fully miscible.

As discussed above, the preferred empirical model accounts for any density changes which occur when the sample is added to the reagent solution and for miscibility, if any, of the sample within the reagent solution. Dilution of the ethanolic reagent solution by a sample on account of the sample's miscibility with the reagent solution may be misinterpreted as consumption of the reagent by acid-base reaction in the reagent-sample mixture, which can lead to a minor overestimation of the acid content of a sample. Thus, the preferred empirical model accounts for this effect by measuring the absorbance of both the reagent solution and the reagent-sample mixture at 1924 cm$^{-1}$ relative to the single-point baseline at 1859 cm$^{-1}$. Absorption at the 1924 cm$^{-1}$ wavelength is measured because interfering absorptions in this region of the IR spectrum are rare. The peak height of the ethanol IR wavelength at 1924 cm$^{-1}$ is measured relative to a baseline at 1859 cm$^{-1}$ ($Abs_{1924/1859\ cm^{-1}}$) in the spectrum of the reagent blank (RB) and in the spectrum of the reagent-sample mixture (S).

The absorption data collected at 1924 cm$^{-1}$ allows for the calculation of a dilution correction factor (DF) for the reagent-sample mixture relative to the reagent solution. The dilution correction factor is calculated by dividing the value of $Abs_{1924/1859}$ cm$^{-1}$ for the reagent blank (RB) by that for the reagent-sample mixture:

$$DF = A_{RB}/A_S \quad (11)$$

where $A_{RB}$ equals the $Abs_{1924/1859\ cm^{-1}}$ value for the reagent blank and $A_S$ is the $Abs_{1924/1859\ cm^{-1}}$ value for the reagent-sample mixture.

The spectrum of the reagent-sample mixture is multiplied by its DF value to obtain the corrected reagent-sample mixture spectrum (Sc):

$$Sc = S*DF \quad (12)$$

where S is the spectrum of the reagent-sample mixture.

The spectrum of the reagent blank (RB) is then subtracted from the corrected reagent-sample mixture spectrum (Sc) to obtain the differential spectrum (Scd):

$$Scd = Sc - RB \quad (13)$$

A 5-5 (gap-segment) 2$^{nd}$ derivative of the differential spectrum (Scd) is then taken (Equations 6-7) and multiplied by 100 to produce the final spectrum (Sf). The $Abs_{2109\ cm^{-1}}$ and $Abs_{1571\ cm^{-1}}$ in this final spectrum (Sf) are then measured.

At block 380, the $Abs_{2109\ cm^{-1}}$ and $Abs_{1571\ cm^{-1}}$ measured in the final spectrum (Se) are placed into the calibration equations (Equations 9 & 10) to determine TUA and OUA, respectively, for the sample. It will be appreciated that the universal calibration equations are used to obtain a good quantification of sample acidity while being independent of the nature of the sample to be analyzed and the volume of reagent solution used in the sample analysis.

Finally, at block 390, the TUA and OUA of the sample are converted to total acid content (TAC) and organic acid content (OAC), respectively:

$$TAC = TUA*V/W \quad (14)$$

$$OAC = OUA*V/W \quad (15)$$

$$IAC = AC - OAC \quad (16)$$

where V is the volume of ethanolic reagent (mL) combined with the sample, W is the weight of the sample (g), and IAC is the inorganic acid content of the sample. These acid content values (TAC, OAC and IAC), multiplied by 56.11 can also be expressed as their corresponding acid number (AN, OAN and IAN) values, terminology with which most analysts are more familiar.

It is noted that when a sample is miscible with the reagent solution, the results of the general analytical test method disclosed herein are potentially subject to matrix effects. In such an event, an optional procedure may be undertaken in which a sample-blank is utilized to correct for such matrix effects as referenced above. When a sample-blank is utilized, the same analytical procedure and calculations (e.g. Equations 11-16) may be employed using the spectrum of the sample-blank. The values obtained in Equations 14-16 for the sample blank may then be subtracted from the corresponding values obtained for the sample to correct the latter for matrix effects.

It is also noted that the method of calibration and analysis disclosed herein can accommodate samples having a wide range of total acid content (TAC) values. The calibration can be tailored to the range of the TAC values likely to be encountered in the samples to be analyzed. For example, as illustrated in Tables 2 and 3 below, three calibration ranges—narrow, medium and wide—are provided to serve as a guide in selecting a suitable calibration range in terms of the expected TAC value (Table 2) and/or in terms of the expected acid number (AN) value (Table 3). The calibration process thus provides the flexibility to accommodate samples having a wide range of TAC values by enabling tailoring of the calibration to the range of TAC values likely to be encountered in the samples to be analyzed.

TABLE 2

| | Preparation of calibration standards | | | | Calculation of TAC range spanned by calibration | | |
|---|---|---|---|---|---|---|---|
| Calibration | OAW range (mg) | R (mL) | $UA_{max}$ (mEq Acid/mL) | $TAC_{max}$ (mEq Acid) | SW (g) | RV (mL) | $SAC_{max}$ (mEq Acid/g) |
| Narrow-range | 0-50 | 15 | 0.01176 | 0.177 | 4 | 15 | 0.0440 |
| Medium-range | 0-100 | 15 | 0.02352 | 0.354 | 4 | 15 | 0.0885 |
| Wide-range | 0-150 | 15 | 0.03456 | 0.531 | 4 | 15 | 0.1327 |

TABLE 3

| | Preparation of calibration standards | | | | Calculation of AN range spanned by calibration | | |
|---|---|---|---|---|---|---|---|
| Calibration | OAW range (mg) | R (mL) | $UA_{max}$ (mg KOH/mL) | $TAN_{max}$ (mg KOH) | SW (g) | RV (mL) | $SAN_{max}$ (mg KOH/g) |
| Narrow-range | 0-50 | 15 | 0.66 | 9.9 | 4 | 15 | 2.47 |
| Medium-range | 0-100 | 15 | 1.32 | 19.9 | 4 | 15 | 4.97 |
| Wide-range | 0-150 | 15 | 1.99 | 29.8 | 4 | 15 | 7.45 |

Table 2 shows, for narrow, medium and wide range AC calibrations, the oleic acid weight (OAW) ranges and reagent solution aliquots (R) which are employed in preparation of the calibration standards discussed above at block 30, as well as the corresponding upper limits of the Unit Acidity ($UA_{max}$) and sample acid content ($SAC_{max}$) values spanned by the calibrations. Table 2 thus serves as a template for the calculation of $SAC_{max}$ values based on the volume of reagent solution (RV) added to a given sample weight (SW) as well as for verifying that the corresponding total acid content ($TAC_{max}$) is within the total acid neutralizing capacity of the ethanolic reagent tabulated in Table 1.

Table 3 also lists narrow, medium, and wide range calibration ranges and the corresponding upper limits of Unit Acidity ($UA_{max}$) expressed in acid number (AN) units together with the corresponding sample AN($SAN_{max}$) values. Table 3 thus serves as a template for the calculation of $SAN_{max}$ values based on the volume of reagent solution (RV) added to a given sample weight (SW) as well as for verification that the corresponding total acid content ($TAN_{max}$) is within the total acid neutralizing capacity of the reagent tabulated in Table 1.

For example, Table 1 indicates that when 15 mL of ethanolic reagent solution is used, the total acid neutralizing capacity of the reagent solution (2.5 g NaHN—C≡N/L) is 0.585 mEq Acid (32.8 mg KOH), and is therefore adequate for these three calibration ranges. However, to stay within the range of any one of these calibrations, samples should be used which have an expected acid content (AC) which is less than SAC. The use of a broader range calibration necessarily implies less analytical sensitivity, and vice versa. It will be appreciated that Table(s) 1-3 may be linked to a pre-programmed Excel spreadsheet which can be used to change the variables of interest interactively to assess other calibration or analytical conditions (e.g. reagent volume, sample weight, etc.) to determine whether such parameters are workable.

While the acidity values in Table-3 are given in AN terms in order to provide a frame of reference with which many analysts are familiar, it will be appreciated that $AC_{pK_a}$ and AN values are not directly comparable, given that AN determinations are based on titration with a much stronger base (KOH) than the base employed in the present method.

It will be appreciated that the methodology disclosed herein provides a number of improvements over earlier methodologies, which employed a two-step analytical protocol in which an oil sample was split into two halves, one-half was mixed with a signal-transducing reagent, the other was mixed with an equal volume of n-propanol, and the measured spectrum of the latter was subtracted from that of the former to produce a differential spectrum representing the spectral changes associated with the acid-base reaction.

Another subsequent methodology utilized a methanolic NaHN—C≡N solution as an alternative to alcoholic KOH rather than as a signal-transducing reagent. However, the latter (but not the former) was precluded, possibly by the instability of NaHN—C≡N in methanol, as evidenced by a progressive decrease of its C≡N band over time, resulting in complete disappearance of this band approximately four days after preparation of the solution, with the concomitant appearance of two new bands at 1650 and 1610 cm$^{-1}$. These spectral changes are believed to have arisen from tautomerization of NaHN—C≡N to an unstable carbodiimide NaN═C═N, and subsequent reaction of this species with methanol to form methyl isourea as discussed in "Automated Acid Content Determination in Lubricants by FTIR Spectroscopy as an Alternative to Acid Number Determination" (Journal of ASTM International, Vol. 6, No. 6, Paper ID JAI102110), which is herein incorporated by reference in its entirety.

As used in the present method, NaHN—C≡N is quite stable in ethanol, an important difference from its observed behavior in methanol. Although the C≡N band in the spectrum of an ethanolic NaHN—C≡N solution shows a gradual decrease over time, the rate at which NaHN—C≡N is depleted in ethanol is much slower than in methanol, taking sixty days to reach completion. Furthermore, the ethanolic solution employed in the present method has been found to be indefinitely stable when stored at freezer temperatures. Consequently, the stability of ethanolic NaHN—C≡N is sufficient to warrant its consideration as a signal-transducing reagent for the determination of acidity in lubricants and edible oils. As discussed above, the principle of this approach is that the absorbance of the strong C≡N band observed at 2109 cm$^{-1}$ in the spectrum of an ethanolic solution of NaHN—C≡N changes proportionately as it is converted to $H_2$N—C≡N by addition of excess acid to the basic solution. The differential spectrum obtained by subtraction of the spectrum of the solution after the addition of acid from the spectrum of the solution before the addition of the acid exhibits a well-isolated and easily measurable NaHN—C≡N band that represents the amount of base consumed by the acid-base reaction. Thus, the acid content of an oil sample can be determined by extraction of the oil with an ethanolic NaHN—C≡N solution of appropriate concentration dependent on the amount of acid in the oil, followed by measurement of the change of the C≡N band in the spectrum of this reagent solution resulting from reaction of NaHN—C≡N with the extracted acids.

Another important consideration relating to the suitability of ethanolic NaHN—C≡N as a reagent for a lubricant FTIR acid content analysis is its basicity. As the only $pK_b$ data available for NaHN—C≡N is a value determined in DMSO, relative $pK_b$ data have been obtained by titrating isomolar ethanolic solutions of NaHN—C≡N and NaOH with 0.1 N HCl. The results have indicated that the $pK_b$ values differed by 1.45 units, with NaHN—C≡N being the weaker base. Thus, in principle, an FTIR acid content method using ethanolic NaHN—C≡N as a base should fully measure the weakest acids of concern from an oil quality standpoint, namely, carboxylic acids, as well as all acids stronger than carboxylic acids.

There have been described and illustrated herein several embodiments of a system and a method of determining organic acid content, inorganic acid content, and total acid content in lubricants, edible oils, and fuels. While particular embodiments of the invention have been described, it is not intended that the invention be limited thereto, as it is intended that the invention be as broad in scope as the art will allow and that the specification be read likewise. Thus, while particular instruments and apparatuses have been disclosed, it will be appreciated that other instruments and apparatuses may be used as well, including various types of computers, spectroscopic analyzers, and manual or automated systems to conduct sample testing to control and/or monitor the quality of a fluid. In addition, while particular quantities and volumes of reagents and samples have been disclosed, it will be appreciated that other quantities and volumes of reagents and samples may be used. While particular method steps for procuring and testing samples have been disclosed, it will be appreciated that certain steps may be omitted from the method, and/or that other steps may be included in the method. Further, while a particular calibration process has been disclosed, it will be appreciated that other calibration processes and empirical modules relating measured absorption changes in the IR wavelengths to acidity of a sample may be utilized. While particular attributes of a sample have been measured and particular equations and calculations have been disclosed based on the measured attributes of the sample for calculating specific parameters of the sample, it will be appreciated that other equations may be utilized, other attributes may be measured, and other parameters may be calculated. While the calculation/generation of acidity data has been disclosed which represents or corresponds to the acid(s) present, including organic acidity, inorganic acidity, total acidity, acid content, organic acid content, inorganic acid content, total acid content, and various unit acidity values, also referred to herein as acidic content and acid content, it will be appreciated that other acidity data for acidic content and acid content may be calculated and that other methods, protocols, empirical models, and calculations may be employed to determine acidity data and acid content. It will therefore be appreciated by those skilled in the art that yet other modifications could be made to the provided invention without deviating from its spirit and scope as claimed.

What is claimed is:

1. A method of characterizing acid content of a lubricant sample, comprising:
    a) providing an ethanolic solution of ethanol and sodium hydrogen cyanamide;
    b) preparing a mixture by adding a first portion of the ethanolic solution to the lubricant sample, wherein sodium hydrogen cyanamide of the ethanolic solution reacts with acidic components of the lubricant sample to form a reaction product that is part of the mixture;
    c) performing infrared spectroscopic testing of the mixture of b) to generate mixture absorption data representing at least one absorption characteristic of the mixture of b), wherein the mixture absorption data includes a first infrared light absorption value of the mixture of b) at a wavelength between 2105 $cm^{-1}$ and 2115 $cm^{-1}$ as well as a second infrared light absorption value of the mixture of b) at a wavelength between 1565 $cm^{-1}$ and 1575 $cm^{-1}$; and
    d) generating acidity data characterizing acid content of the lubricant sample based on the mixture absorption data of c), wherein the acidity data is based upon at least one calibration equation relating the mixture absorption data to acidity of the lubricant sample.

2. A method according to claim 1, wherein:
the acidity data for the lubricant sample in d) characterizes the total acid content of the lubricant sample.

3. A method according to claim 1, wherein:
the acidity data for the lubricant sample in d) characterizes organic acid content of the lubricant sample.

4. A method according to claim 1, wherein:
the acidity data for the lubricant sample in d) characterizes inorganic acid content of the lubricant sample.

5. A method according to claim 1, wherein:
the calibration equation is based upon an empirical model derived from a calibration protocol.

6. A method according to claim 5, wherein:
the calibration protocol includes preparing a plurality of calibration standards and performing infrared spectroscopic testing of the plurality of calibration standards to generate calibration data representing an absorption characteristic of each of the plurality of calibration standards.

7. A method according to claim 6, wherein:
preparing the calibration standards includes adding additional portions of the ethanolic solution to corresponding portions of an organic acid.

8. A method according to claim 7, wherein:
the additional portions of the ethanolic solution contain an equal amount of the ethanolic solution, and the corresponding portions of organic acid contain different amounts of the organic acid.

9. A method according to claim 7, wherein:
the organic acid is a carboxylic acid.

10. A method according to claim 7, wherein:
the calibration protocol includes calculating a density correction factor for each calibration standard, the density correction factor accounting for changes to the absorption characteristic of each of the plurality of calibration standards caused by a change in density during formation of each calibration standard when a respective portion of the ethanolic solution is added to a corresponding portion of the organic acid.

11. A method according to claim 10, wherein:
the density correction factor is calculated from a measured value of the absorption characteristic of each calibration standard at an infrared wavelength of 1924 $cm^{-1}$.

12. A method according to claim 10, wherein:
the calibration data includes a measured infrared spectrum corresponding to each calibration standard, and the density correction factor is used to calculate a corrected calibration spectrum corresponding to each calibration standard, the corrected calibration spectrum for a given calibration standard calculated as the product of the measured infrared spectrum of the given calibration standard and the density correction factor for the given calibration standard.

13. A method according to claim 12, wherein:
the mixture absorption data includes an absorption spectrum corresponding to the reagent-sample mixture, and the calibration protocol includes calculating a differential spectrum for each calibration standard by subtracting the absorption spectrum of the reagent solution from the corrected calibration spectrum of each calibration standard.

14. A method according to claim 13, wherein:
the calibration protocol includes calculating a 5-5 gap-segment second derivative of the differential spectrum of each calibration standard.

15. A method according to claim 6, wherein:
the calibration data generated during the calibration protocol includes an absorption value of each calibration standard at an infrared wavelength of 2109 cm$^{-1}$.

16. A method according to claim 15, wherein:
at least one calibration equation is derived from the absorption values of the calibration standards at the infrared wavelength of 2109 cm$^{-1}$.

17. A method according to claim 6, wherein:
the calibration data generated during the calibration protocol includes an absorption value of each calibration standard at an infrared wavelength of 1571 cm$^{-1}$.

18. A method according to claim 17, wherein:
at least one calibration equation is derived from the absorption values of the calibration standards at the infrared wavelength of 1571 cm$^{-1}$.

19. A method according to claim 1, wherein:
the acidity data for the lubricant sample in d) characterizes inorganic acid content of the lubricant sample.

20. A method according to claim 1, wherein:
the at least one calibration equation is independent of concentration of both the lubricant sample and the ethanolic solution in the mixture of b).

21. A method of characterizing acid content of a lubricant sample, comprising:
a) providing an ethanolic solution of ethanol and sodium hydrogen cyanamide;
b) preparing a mixture by adding a first portion of the ethanolic solution to the lubricant sample, wherein sodium hydrogen cyanamide of the ethanolic solution reacts with acidic components of the lubricant sample to form a reaction product that is part of the mixture;
c) performing infrared spectroscopic testing of the mixture of b) to generate mixture absorption data representing at least one absorption characteristic of the mixture of b), wherein the mixture absorption data includes a first infrared light absorption value of the mixture of b) at a wavelength between 2105 cm$^{-1}$ and 2115 cm$^{-1}$ as well as a second infrared light absorption value of mixture of b) at a wavelength between 1565 cm$^{-1}$ and 1575 cm$^{-1}$; and
d) generating acidity data that characterizes acid content of the lubricant sample based on the mixture absorption data of c) by employing a calibration protocol which utilizes an empirical model to determine at least one calibration equation relating the mixture absorption data of c) to acidity of the lubricant sample,
wherein the calibration protocol includes preparing a plurality of calibration standards by adding additional portions of the ethanolic solution to corresponding portions of an acid, and performing infrared spectroscopic testing of the plurality of calibration standards to generate calibration data representing an absorption characteristic of each of the plurality of calibration standards.

22. A method according to claim 21, wherein:
the calibration data generated during the calibration protocol includes an absorption value of each calibration standard at an infrared wavelength of 2109 cm$^{-1}$, and an absorption value of each calibration standard at an infrared wavelength of 1571 cm$^{-1}$.

23. A method according to claim 22, wherein:
a first calibration equation of the empirical model is derived from the absorption values of the calibration standards at the infrared wavelength of 2109 cm$^{-1}$, and a second calibration equation of the empirical model is derived from the absorption values of the calibration standards at the infrared wavelength of 1571 cm$^{-1}$.

24. A system according to claim 21, wherein:
the acidity data for the lubricant sample in d) characterizes the total acid content of the lubricant sample.

25. A method according to claim 21, wherein:
the acidity data for the lubricant sample in d) characterizes organic acid content of the lubricant sample.

26. A method according to claim 21, wherein:
the at least one calibration equation is independent of concentration of both the lubricant sample and the ethanolic solution in the mixture of b).

27. A system for characterizing a mixture of a lubricant sample and a solution of ethanol and sodium hydrogen cyanamide, wherein sodium hydrogen cyanamide of the solution reacts with acidic components of the lubricant sample to form a reaction product that is part of the mixture, the system comprising:
a cell for holding and evaluating the mixture;
an infrared spectrometer for measuring light absorption characteristics of the mixture and outputting mixture absorption data representing the light absorption characteristics of the reagent-sample mixture, wherein the mixture absorption data includes a first infrared light absorption value of the mixture at a wavelength between 2105 cm$^{-1}$ and 2115 cm$^{-1}$ as well as a second infrared light absorption value of the mixture at a wavelength between 1565 cm$^{-1}$ and 1575 cm$^{-1}$; and
a data processing system configured to input and analyze the mixture absorption data from the infrared spectrometer and generate acidity data that characterizes the acid content of the lubricant sample based on the mixture absorption data, wherein the acidity data is based upon at least one calibration equation relating the mixture absorption data to acidity of the lubricant sample.

28. A system according to claim 27, wherein:
the data processing system is configured to interact with a user to employ a calibration protocol that uses an empirical model to determine the at least one calibration equation.

29. A system according to claim 28, wherein:
the calibration protocol includes analyzing calibration data representing light absorption characteristics of each of a plurality of calibration standards measured by the infrared spectrometer, the calibration standards prepared from additional portions of the ethanolic solution added to corresponding portions of an organic acid.

30. A system according to claim 29, wherein:
the data processing system is configured to calculate a density correction factor and a corrected calibration spectrum for each calibration standard based on the calibration data.

31. A system according to claim 30, wherein:
the data processing system is configured to calculate a differential spectrum for each calibration standard and a 5-5 gap-segment second derivative for each differential spectrum.

32. A system according to claim 27, wherein:
the acidity data for the lubricant sample generated by the data processing system characterizes the total acid content of the lubricant sample.

33. A system according to claim 27, wherein:
the acidity data for the lubricant sample generated by the data processing system characterizes organic acid content of the lubricant sample.

34. A system according to claim 27, wherein:
the acidity data for the lubricant sample generated by the data processing system characterizes inorganic acid content of the lubricant sample.

35. A system according to claim 27, wherein:
the at least one calibration equation is independent of concentration of both the lubricant sample and the ethanolic solution in the mixture.

\* \* \* \* \*